United States Patent
Tuck

(10) Patent No.: US 6,923,181 B2
(45) Date of Patent: Aug. 2, 2005

(54) NASAL MASK

(75) Inventor: Winton Charles Tuck, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 71 days.

(21) Appl. No.: 10/180,714

(22) Filed: Jun. 26, 2002

(65) Prior Publication Data

US 2003/0000531 A1 Jan. 2, 2003

(30) Foreign Application Priority Data

Jun. 27, 2001 (NZ) .............................................. 512649

(51) Int. Cl.$^7$ ................................................ A62B 9/02
(52) U.S. Cl. ......................... 128/205.24; 128/206.21; 128/207.12; 137/512.15
(58) Field of Search ....................... 128/204.18, 204.29, 128/205.24, 207.12, 204.26, 206.21, 204.24, 204.23; 137/512.15, 855

(56) References Cited

U.S. PATENT DOCUMENTS

| | | | | |
|---|---|---|---|---|
| 3,769,973 A | * | 11/1973 | Esbenshade, Jr. ...... | 128/200.14 |
| 3,874,378 A | * | 4/1975 | Issacson et al. ....... | 128/205.24 |
| 4,316,458 A | | 2/1982 | Hammerton-Fraser | |
| 5,538,000 A | | 7/1996 | Rudolph | |
| 5,647,355 A | * | 7/1997 | Starr et al. ............. | 128/205.24 |
| 5,655,520 A | * | 8/1997 | Howe et al. ........... | 128/203.12 |
| 5,662,101 A | * | 9/1997 | Ogden et al. .......... | 128/205.25 |
| 5,791,339 A | * | 8/1998 | Winter ................... | 128/202.22 |
| 5,896,857 A | * | 4/1999 | Hely et al. ............. | 128/205.24 |
| 6,006,748 A | * | 12/1999 | Hollis .................... | 128/205.24 |
| 6,073,630 A | * | 6/2000 | Adahan ................. | 128/205.24 |
| 6,513,519 B2 | * | 2/2003 | Gallem .................. | 128/200.14 |

FOREIGN PATENT DOCUMENTS

| | | |
|---|---|---|
| CH | 345118 | 4/1960 |
| EP | 0549299 | 12/1992 |
| FR | 2535613 | 5/1984 |
| WO | WO 0038772 | 7/2000 |
| WO | WO 02062413 | 8/2002 |

\* cited by examiner

*Primary Examiner*—Glenn K. Dawson
*Assistant Examiner*—Darwin P Erezo
(74) *Attorney, Agent, or Firm*—Trexler, Bushnell, Giangiorgi, Blackstone & Marr, Ltd.

(57) ABSTRACT

A system is disclosed comprising a high pressure gases source: for example a compressor, a low cross section conduit adapted to convey gases from the compressor, and a patient interface delivering gases to the patient. The patient interface includes valve member which is substantially closed during inspiration and venting externally during expiration. The combination of the low cross section and lightweight conduit and the valve member result in increased patient comfort.

13 Claims, 4 Drawing Sheets

NASAL MASK

FIELD OF INVENTION

This invention relates to patient interfaces particularly though not solely for use in delivering CPAP therapy to patients suffering from obstructive sleep apnoea (OSA).

BACKGROUND ART

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

Where such masks are used in respiratory therapy, in particular treatment of Obstructive Sleep Apnea (OSA) using Continuance Positive Airway Pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. The washout of gas from the mask is essential to ensure the carbon dioxide build up does not occur over the range of flow rates. In the typical values of pressure in CPAP treatment, usually between 4 cm $H_2O$ to 20 cm $H_2O$, prior art attempts at such vents have resulted in patient discomfort due to the effort required to breath out against the positive pressure.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the invention consists in a device for delivering a supply of gases to a user comprising a patient interface, in use in fluid communication with said supply of gases, engaging with said user and thereby supplying said gases to said user; and outlet means being integrated with or in fluid communication with said patient interface, said outlet means comprising:

a valve body including an internal passage, in use at least a portion of said gases flowing through said internal passage, an external vent, and a valve member operatively connected to said valve body and having at least two configurations, a first configuration in use during inspiration of said patient substantially blocking said vent and a second configuration in use with said vent passing expired gases from said patient.

Preferably said device further comprising biasing means adapted to retain or actuate said valve member between said first configuration and said second configuration.

Preferably said biasing means adapted to retain or actuate said valve member depending on the flow rate of gases through said internal passage.

Preferably said biasing means comprises a venturi in said internal passage including an outlet in use incident on said valve member.

Preferably said valve member comprises a flap of flexible material.

Preferably said flexible material is a rubber composition.

Preferably said vent is a passage through said valve body from the interior of said patient interface to the exterior.

Preferably said patient interface is a nasal mask.

Preferably said nasal mask comprising:

restraining means attached to or around the head of said user, a body portion having an inlet receiving said supply of gases and an open section, sealing means attached to said body portion substantially contoured to the facial contours of said user, receiving means attached to said hard body which in use engages with said restraining means.

In a second aspect the present invention consists in a valve for use with a patient interface, for delivering breathing assistance in the form of gases to a patient, said valve being integrated with or in fluid communication with said patient interface, said valve comprising:

a valve body including an internal passage, in use at least a portion of said gases flowing through said internal passage, an external vent, and a valve member operatively connected to said valve body and having at least two configurations, a first configuration in use during inspiration of said patient substantially blocking said vent and a second configuration in use with said vent passing expired gases from said patient.

Preferably said valve further comprising biasing means adapted to retain or actuate said valve member between said first configuration and said second configuration.

Preferably said biasing means adapted to retain or actuate said valve member depending on the flow rate of gases through said internal passage.

Preferably said biasing means comprises a venturi in said internal passage including an outlet in use incident on said valve member.

Preferably said valve member comprises a flap of flexible material.

Preferably said flexible material is a rubber composition.

Preferably said vent is a passage through said valve body from the interior of said patient interface to the exterior.

In a third aspect the present invention consists in a system for delivering respiratory gases to a user comprising:

a high pressure gases sources, a low cross section conduit adapted to convey gases from said gases source, and a patient interface adapted to deliver gases from said conduit to said patient.

Preferably said patient interface further comprises a valve member operatively connected to said patient interface and having at least two configurations, a first configuration in use during inspiration of said patient substantially closed and a second configuration in use externally venting expired gases from said patient.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides improvements in the delivery of CPAP therapy. In particular a patient interface is described which is quieter for the user to wear and reduces the side leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks and mouthpieces.

Figure 1:
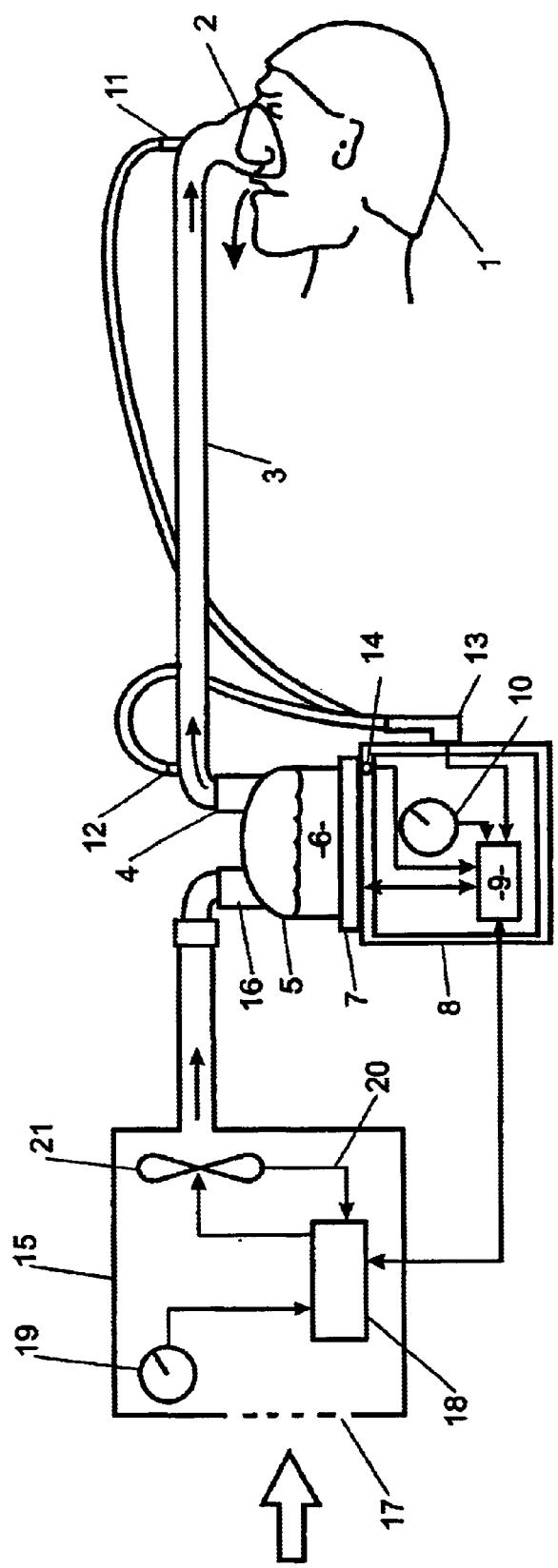
FIG. 1 is a block diagram of a humidified continuous positive airway pressure (system) as might be used in conjunction with the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit Humidification chamber 6 is preferably formed from a plastics material and may have a highly heat conductive base (for example an aluminum base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

In one preferred embodiment inspiratory conduit 3 is characterised by a small cross section, having much reduced weight to conduits normally used in the art of breathing assistance. For example preferably the internal diameter of the small cross section conduit is 4 to 6 mm. Preferably the tubing is constructed of plastic or other compositions to allow the conduit to be relatively flexible. In order to overcome the increased resistance of the conduit (normally respiratory conduit is of the order of 20 mm internal diameter), blower 15 preferably comprises a variable pressure compressor able to deliver high pressures at flow rates common with methods of breathing assistance eg: 50–80 l/min. For example preferably the compressor is capable of delivering 3 bar or 3000 cm $H_2O$ at its source.

Less preferably blower 15 is provided with variable pressure regulating means (eg: valve and fixed speed fan) or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
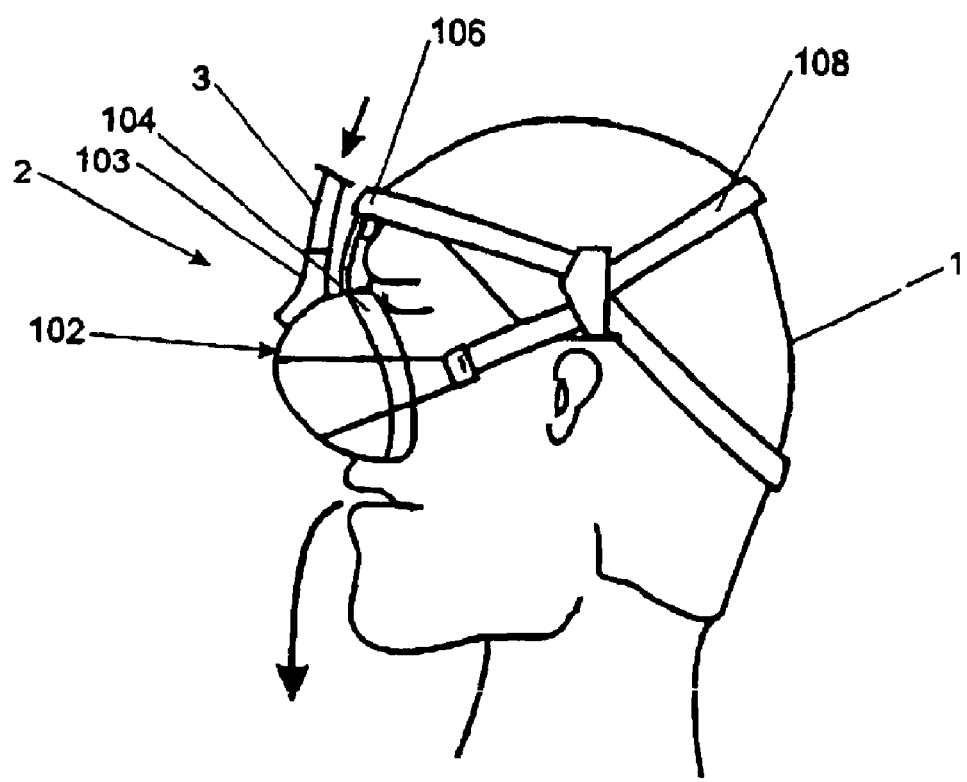
FIG. 2 is an illustration of the nasal mask in use according to the preferred embodiment of the present invention.

According to a first embodiment of the present invention the patient interface is shown in FIG. 2 as a nasal mask. The mask includes a hollow body 102 with a manifold 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Outlet Valve

Figure 4:
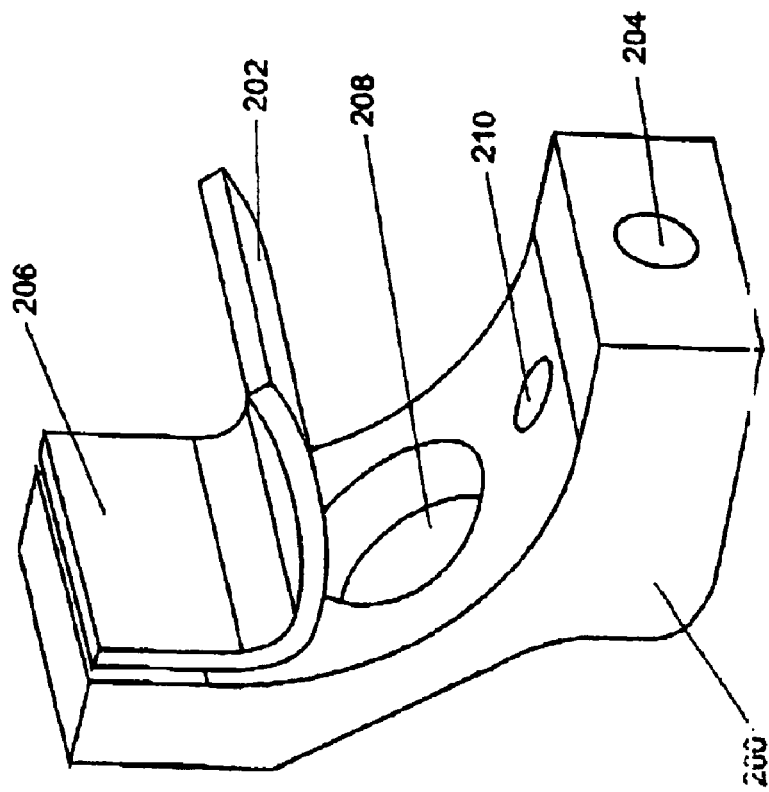
FIG. 4 is a perspective view of the outlet valve in the open condition.
Figure 3:
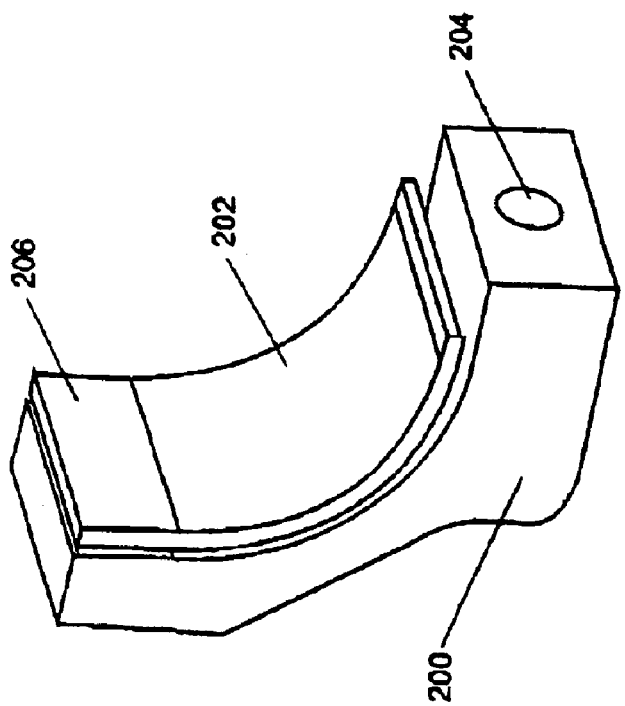
FIG. 3 is a perspective view of the outlet valve in the closed condition.
Figure 5:
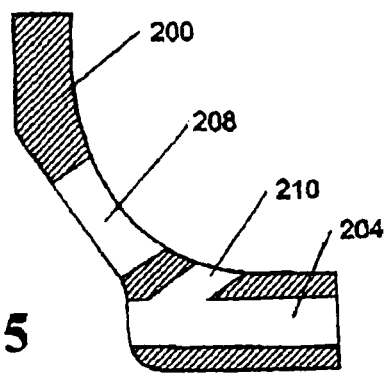
FIG. 5 is a cutaway view of the valve.

Referring now to FIGS. 3 to 5 the manifold (103, FIG. 2) as described according to the preferred embodiment of the present invention. The manifold includes a valve body 200, and inlet passage 204 and an outlet vent 208. Gases from the conduit (3, FIGS. 1, 2) flow in through the inlet passage into the mask on inspiration and out from the mask through the outlet vent 208 on expiration. A sealing flap 202 is attached at one end 206 to the valve body, and seals over the outlet vent 208.

In the preferred embodiment of the present invention the sealing flap 202 is biased closed against the outlet vent 208 by a venturi passage 210 in the inlet passage 204. The outlet of the venturi passage 210 is near the free end of the sealing flap 202. During inspiration the flow through the inlet passage 204 causes a negative pressure in the venturi passage 210, which holds the sealing flap closed, as shown in FIG. 3, against the outlet vent 208.

During expiration, as shown in FIG. 4, the flow in inlet passage 204 stops, removing the negative pressure from the venturi 210, allowing the sealing flap 202 to open. The expired gases then flow out the outlet vent 208. In a further embodiment the venturi effect could be achieved using normal cross section respiratory conduit and providing a constriction at or about the venturi passage 210.

It will also be appreciated that the retaining of the flap in either position could equally be provided through any mechanical or electronic mechanism. For example the sealing flap could comprise a piezoelectric valve member.

Figure 6:
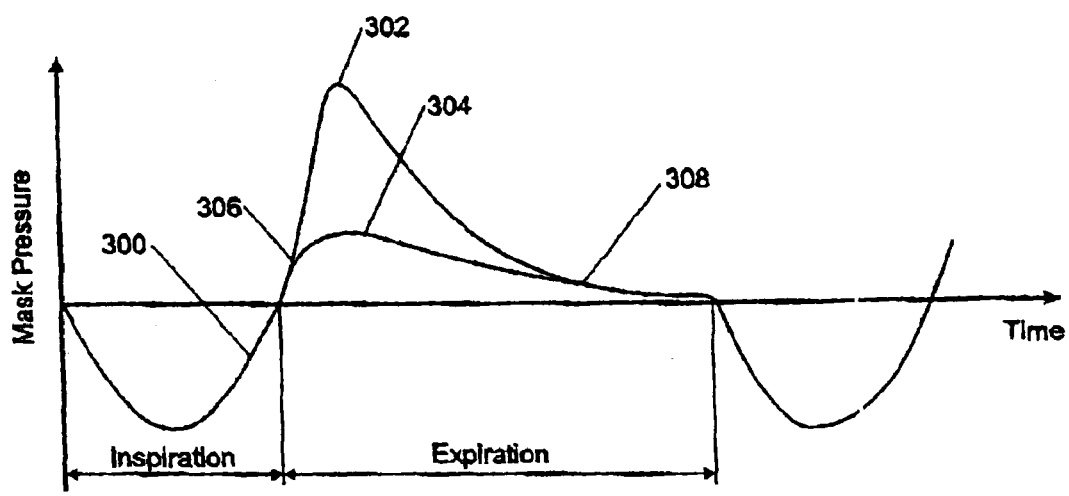
FIG. 6 is a pressure graph according to the preferred embodiment of the present invention.

This process is illustrated in FIG. 6 with the pressure profile of a prior art mask compared with the present invention, where the horizontal axis lies about the mean positive pressure. During inspiration 300 the two systems are identical. During expiration the present invention 304 has a lower peak expiratory pressure compared with the prior art 302. The difference is explained by the lower resistance of the large outlet vent, as the sealing flap opens 306 near the beginning of expiration, and closes 308 near the end of expiration.

As has been described above the present invention provides improved venting of expired gases over prior art masks. In particular the use of the small cross section conduit maximises patient comfort and compliance. The small cross section makes buffering of expired gases, i.e. allowing them to flow partly back up the inspiratory conduit, less effective when compared with a larger cross section conduit. Accordingly the present invention outlet vent provides effective $CO_2$ washout, and reduced patient effort in breathing out, improving patient comfort.

What is claimed is:

1. A device for delivering a supply of gases to a user comprising a patient interface, in use in fluid communication with said supply of gases, engaging with said user and thereby supplying said gases to said user; and outlet means being integrated with or in fluid communication with said patient interface, said outlet means comprising:

a valve body including an internal passage, in use at least a portion of said gases flowing through said internal passage, an external vent, and a flexible flap operatively connected to said valve body and having at least two configurations, a first configuration in use during inspiration of said patient substantially blocking said vent and a second configuration in use with said vent passing expired gases from said patient, said flexible flap externally connected to said valve body, a biasing means adapted to retain or actuate said flexible flap between said first configuration and said second configuration, wherein said biasing means is a venturi in said internal passage.

2. A device as claimed in claim 1 wherein said biasing means adapted to retain or actuate said valve member depending on th flow rate of gases through said internal passage.

3. A device as claimed in claim 2 wherein said venturi in said internal passage includes an outlet in use incident on said valve member.

4. A device as claimed in claim 1 wherein said flexible material is a rubber composition.

5. A device as claimed in claim 1 wherein said vent is a passage through said valve body from the interior of said patient interface to the exterior.

6. A device as claimed in claim 1 wherein said patient interface is a nasal mask.

7. A device as claimed in claim 6 wherein said nasal mask comprising:

restraining means attached to or around the head of said user, a body portion having an inlet receiving said supply of gases and an open section, sealing means attached to said body portion substantially contoured to the facial contours of said user, receiving means attached to said hard body which in use engages with said restraining means.

8. A valve for use with a patient interface, for delivering breathing assistance in the form of gases to a patient, said valve being integrated with or in fluid communication with said patent interface, said valve comprising:

a valve body including an internal passage, in use at least a portion of said gases flowing through said internal passage, an external vent, and a flexible flap operatively connected to said valve body and having at least two configurations, a first configuration in use during inspiration of said patient substantially blocking said vent and a second configuration in use with said vent passing expired gases from said patient, said flexible flap externally connected to said valve body, a biasing means adapted to retain or actuate said flexible flap between said first configuration and said second configuration, wherein said biasing means is a venturi in said internal passage.

9. A valve as claimed in claim 8 wherein said biasing means adapted to retain or actuate said valve member depending on the flow rate of gases through said internal passage.

10. A valve as claimed in claim 9 wherein said venturi in said internal passage includes an outlet in use incident on said valve member.

11. A valve as claimed in claim 8 wherein said flexible material is a rubber composition.

12. A valve as claimed in claim 8 wherein said vent is a passage through said valve body from the interior of said patient interface to the exterior.

13. A system for delivering respiratory gases to a user comprising:

a high pressure gases source, a low cross section conduit adapted to convey gases from said gases source, a patient interface including an internal passage and adapted to deliver gases from said conduit to said patient, and a flexible flap operatively connected to said patient interface and having at least two configurations, a first configuration in use during inspiration of said patient substantially closed and a second configuration in use externally venting expired gases from said patient said flexible flap externally connected to said valve body, a biasing means adapted to retain or actuate said flexible flap between said first configuration and said second configuration, wherein said biasing means is a venturi in said internal passage.

* * * * *